United States Patent [19]

Karapita

[11] Patent Number: 4,592,527

[45] Date of Patent: Jun. 3, 1986

[54] OVERHEAD TROLLEY

[76] Inventor: Alexander D. Karapita, 38 Robinter Drive, Willowdale, Ontario, Canada, M2M 3R2

[21] Appl. No.: 491,348

[22] Filed: May 4, 1983

Related U.S. Application Data

[63] Continuation-in-part of Ser. No. 207,227, Nov. 17, 1980, abandoned.

[51] Int. Cl.[4] .............................................. A47H 1/10
[52] U.S. Cl. .................................... 248/318; 211/113
[58] Field of Search ................ 248/323, 318; 211/113, 211/162, 117; 104/93, 106, 107, 108, 109; 188/43; 17/24; 105/151

[56] References Cited

U.S. PATENT DOCUMENTS

| | | | |
|---|---|---|---|
| 385,493 | 7/1888 | Wood | 248/323 |
| 812,396 | 2/1906 | Bewyer | 211/117 X |
| 927,082 | 7/1909 | Smalley | 211/117 X |
| 1,796,243 | 3/1931 | Coughlin | 24/27 |
| 1,846,537 | 2/1932 | Withrow | 105/151 X |
| 2,148,515 | 2/1939 | Taylor | 16/103 X |
| 2,435,755 | 2/1948 | Schimpff | 211/117 X |
| 2,718,852 | 9/1955 | Cacciatore | 104/93 X |
| 2,814,457 | 11/1957 | Phelan | 248/328 |
| 2,953,116 | 9/1960 | Lund | 105/151 X |
| 3,006,481 | 10/1961 | Gussack | 211/117 |
| 3,191,903 | 6/1965 | Wieland | 248/328 |
| 3,321,090 | 5/1967 | Greenstadt | 211/162 |
| 3,944,180 | 3/1976 | Rogers | 248/323 |

FOREIGN PATENT DOCUMENTS 417688 10/1934 United Kingdom .................. 104/93

Primary Examiner—J. Franklin Foss

[57] ABSTRACT

A trolley for suspending a weight from an overhead track having a pair of spaced, parallel rails or comprising an I beam. The trolley comprises a pair of slide members slidable along the track; friction elements locatable below the track; and arms interconnecting the slide members and the friction elements to suspend a weight therefrom whereby on suspension of a weight from the interconnecting arms at least the friction elements are moved towards the track to lock the trolley in a preselected position along the track.

20 Claims, 12 Drawing Figures

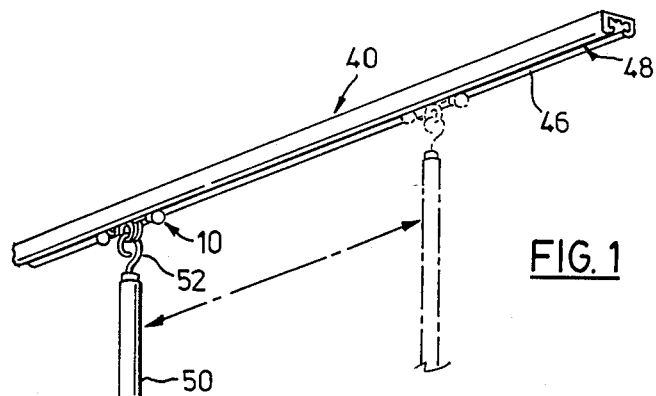
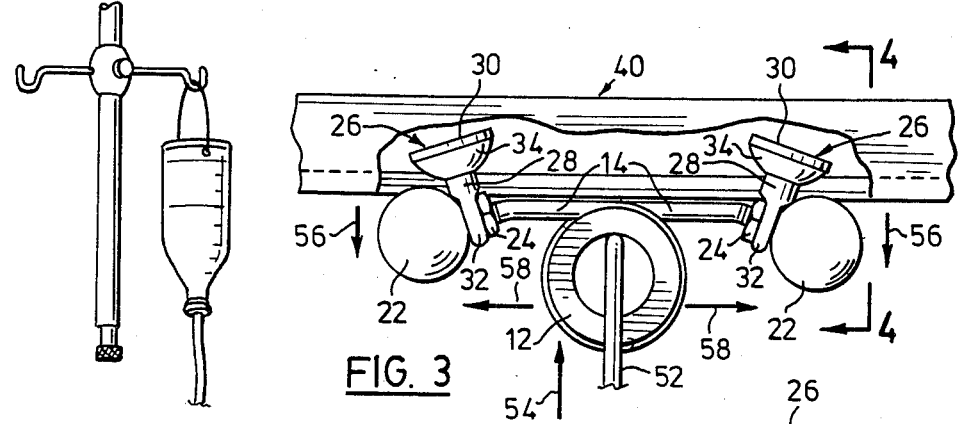
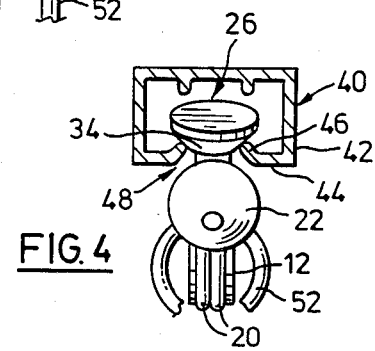
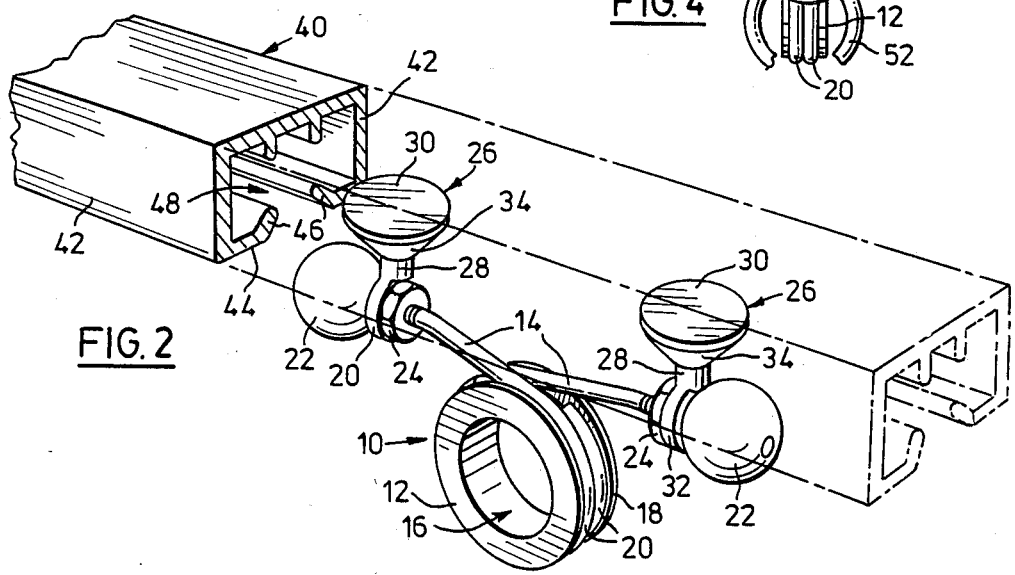

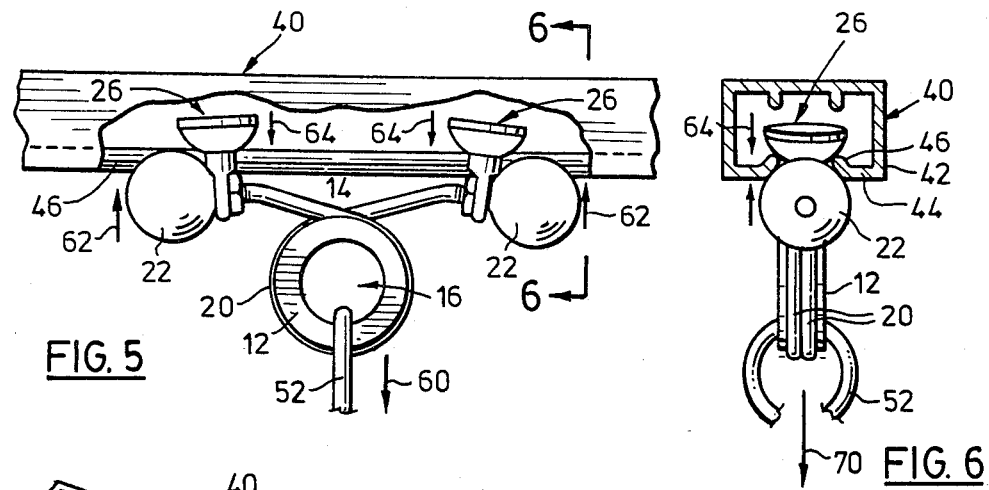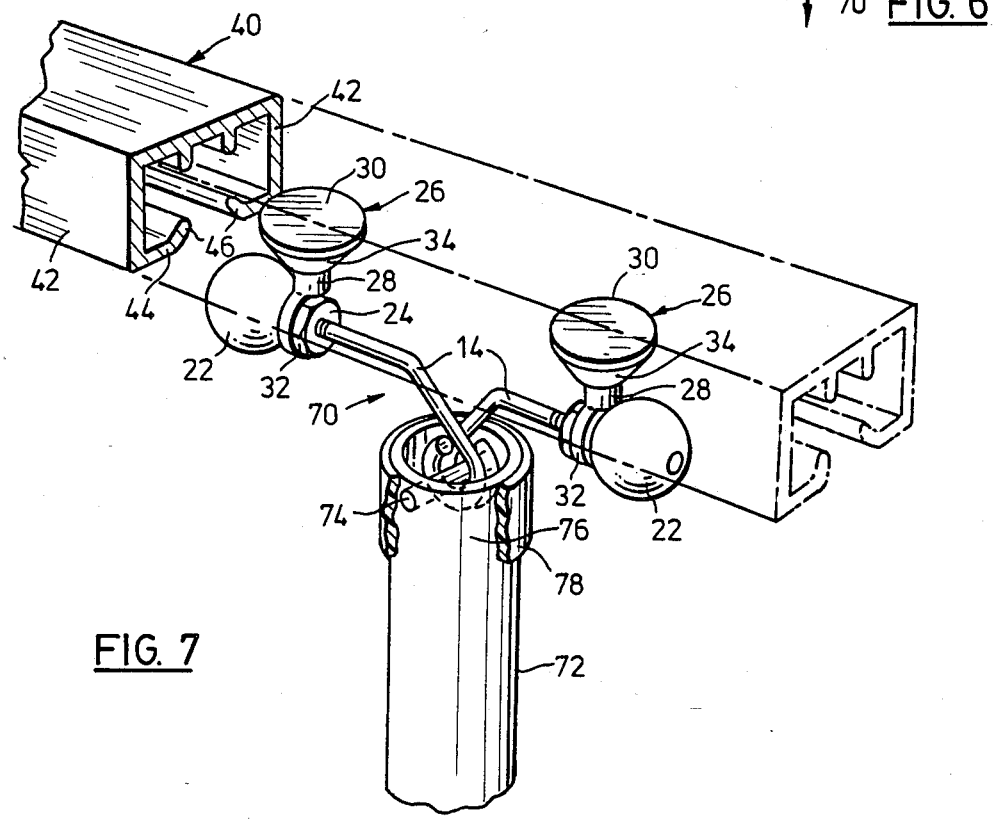

OVERHEAD TROLLEY

This is a continuation-in-part of U.S. patent application Ser. No. 207,227 filed Nov. 17, 1980 in the name of Alexander Donald Karapita entitled Overhead Trolley, now abandoned.

FIELD OF THE INVENTION

This invention relates to a trolley for use in suspending articles, such as intravenous bottles, from an overhead track.

BACKGROUND OF THE INVENTION

Mobile suspension systems for such a purpose are known in which a supporting apparatus runs along an overhead track and a simple example is disclosed in U.S. Pat. No. 3,006,481 issued Oct. 31, 1961 in the name of Nathan A. Gussack. Since such a device will move along the track when touched or when the track is slightly sloped, it is advantageous to be able to lock the device in one position on the track when it is in use. A supporting apparatus having a locking device is disclosed in U.S. Pat. No. 3,321,090 issued May 23, 1967 in the name of J. C. Greenstad. The Greenstadt device has the advantage that it locks in place on the track when a weight is suspended from it but it has a number of working parts which makes it relatively complex in construction and expensive to manufacture and susceptible to breakdown.

It is an object of the present invention to provide an improved hanger which is of simplified construction and more reliable in operation.

SUMMARY OF THE INVENTION

Essentially the invention consists of a trolley for suspending a weight from an overhead track, comprising: means locatable above the track and slidable along the track; friction means locatable below the track; and means interconnecting the slidable means and the friction means to suspend a weight therefrom and to provide a moment couple between the slidable means and the friction means about the track, whereby on suspension of a weight from the interconnecting means at least the friction means is moved towards the track to lock the trolley in a preselected position along the track.

BRIEF DESCRIPTION OF THE DRAWINGS

Example embodiments of the invention are shown in the accompanying drawings in which:

FIG. 1 is a perspective view of a trolley mounted on an overhead track and supporting a weight;

FIG. 2 is a detailed perspective view of the trolley of FIG. 1 in relation to the track;

FIG. 3 is a side view in elevation of the trolley and track of FIGS. 1 and 2;

FIG. 4 is a cross-sectional view taken along line 4—4 of FIG. 3;

FIG. 5 is a view similar to FIG. 3 showing the trolley in locked position on the track;

FIG. 6 is a cross-sectional view taken along line 6—6 of FIG. 5;

FIG. 7 is a perspective view similar to FIG. 3 showing an alternate embodiment of the invention;

DETAILED DESCRIPTION OF PREFERRED EMBODIMENTS

Figure 8:
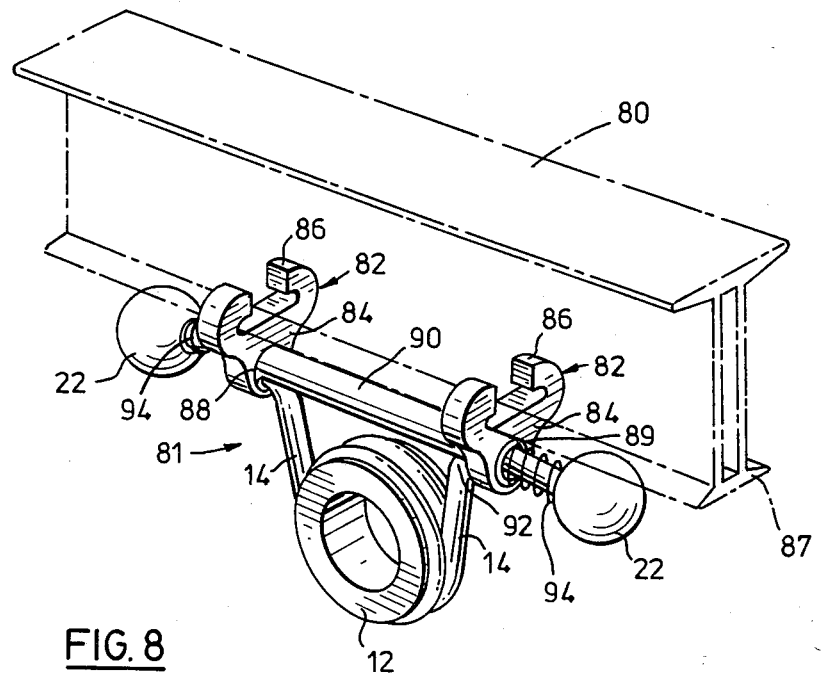
FIG. 8 is a perspective view of an alternate embodiment of a trolley mounted on a single overhead track.

The example embodiment shown in FIGS. 1 to 6 of the drawings consists of a trolley 10 having an axle member of ring 12 and a pair of opposed arms 14 extending tangentially from the ring. Ring 12 has a central aperture 16 and a circumferential recess or groove 18 on its outer periphery. One end of each arm 14 carries an annular member in the form of a loop 20 and the two loops are located side by side in groove 18 of ring 12 and slidable in the groove about the axis of the ring.

Each arm 14 remote from loop 20 terminates in a spherical friction element 22 which is preferably threaded onto the end of the arm. A nut 24 is threaded on arm 14 adjacent friction element 22 and holds a slide member 26 which consists of a shank 28 lying in the plane of loop 20 and a head 30. Shank 28 carries an eye 32 which is loosely engaged by arm 14 and held against friction element 22 by nut 24. Head 30 tapers inwardly to meet shank 28, which provides a bevelled circumferential bearing surface 34 giving a wedge contour in cross-section.

Trolley 10 rests on an overhead track 40 which is of inverted U-shape in cross-section with downwardly extending side walls 42 terminating in inwardly directed flanges 44 which are angled upwardly at their free edges to form a pair of parallel, spaced rails 46 defining a central slot 48. Bearing surfaces 34 of slide members 26 of trolley 10 rest on rails 46 with heads 30 located within track 40 and ring 12, together with arms 14 and friction element 22, located beneath the track, as seen in FIGS. 3 and 4 of the drawings.

In the operation of the device shown in FIGS. 1 to 6 of the drawings, a weight is supportable by trolley 10 through ring 12. In the illustrated embodiment this weight is in the form of a hanger 50 which is an adjustable intravenous pole having a hook 52 which is engagable with ring 12 of trolley 10. To move hanger 50 along the track, as seen in FIG. 1, the hanger is moved upwardly in the direction of arrow 54 to have hook 52 move ring 12 upwardly in the direction of track 40 as seen in FIG. 3. As ring 12 moves upwardly, loops 20 of arms 14 rotate in groove 18 of the ring and friction element 22 move downwardly in the direction of arrows 56 out of contact with rails 46, allowing trolley 10 to be moved freely along the rails in the direction of arrows 58 by the imposition of lateral pressure on hanger 50. When the weight of hanger 50 is being carried by trolley 10, ring 12 is pulled downwardly in the direction of arrow 60 as seen in FIGS. 5 and 6 of the drawings which causes friction elements 22 to be pulled upwardly in the direction of arrows 62 until the friction elements wedge into slot 48 between rails 46 whereupon the trolley is locked in position on the track. In this position heads 26 wedge downwardly into slot 48 between rails 46 in the direction of arrows 64 to reinforce the locking action of friction elements 22 by providing a moment couple between each head and its associated friction element.

Because slide members 26 are loosely mounted on arms 14 by shanks 28 and eyes 32, a weight suspended from trolley 10 may be swung laterally, i.e. transverse to a vertical plane of loops 20 apart from any pivotal action of the means engaging the weight with ring 12. In this lateral swinging action arms 14 axially rotate in eyes 32.

In the alternate embodiment shown in FIG. 7 of the drawings a trolley 70 is incorporated in a hanger 72 at its upper end. In this embodiment loops 20 loosely encircle a pin 74 which is mounted transversely in the open end portion 76 of hanger 72 by a press fitted sleeve 78. The operation of the device of FIG. 7 is the same as that of the device of FIGS. 1 to 6.

Figure 11:
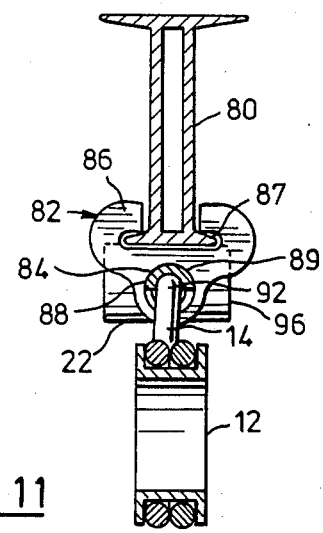
FIG. 11 is a cross-sectional view taken along line 11—11 of FIG. 10.

It will be appreciated that slide members 26 could be of any configuration to bridge slot 48 between rails 46 but they are preferably bevelled to provide additional wedging action between the rails when trolley 10 is locked on track 40. Similarly friction members 22 could be of any configuration to bridge slot 48 but an upward wedging action between rails 46 is preferred. For example slide members 26 and friction elements 22 might be bridging elements to accommodate heavier weights without distorting rails 46 laterally (see FIGS. 11 and 12), the locking action being provided by the coupling moment generated by the downward tilting of each arm 14 when a weight is suspended from ring 12.

In the alternate embodiment shown in FIGS. 8 to 12 of the drawings rails 46 of track 40 are replaced by an I beam 80 and in a trolley 81 slide members 26 are replaced by a pair of slide members 82 which each comprise a body 84 having a pair of upwardly and inwardly hooked arms 86 which engage the lower flange 87 of I beam 80 and an aperture 88. Bodies 84 are preferably interconnected by a spacer bar 90. Also, opposed arms 14 extending tangentially from ring 12 are directed upwardly at a steep angle in relation to I beam 80 and the arms each have a sharp elbow 92 adjacent the associated slide member 84 redirecting the arm through aperture 88 of the slide member. Each arm carries a coaxial compression spring 94, one end of the spring bearing against slide member 84 and the other end bearing against spherical friction element 22. Each aperture 88 may have a bearing sleeve lining 89 which may be a separate element or integral with spacer bar 90 as shown in FIG. 8.

Figure 9:
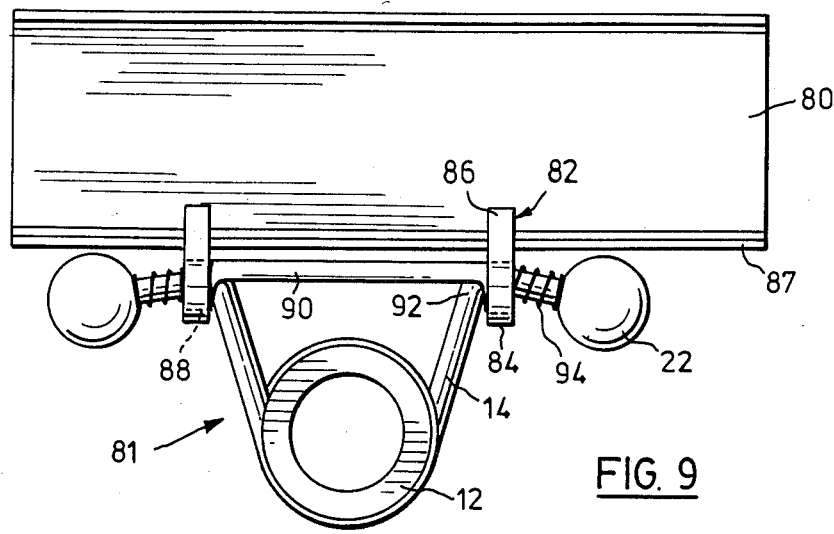
FIG. 9 is a side view, in elevation, of the trolley of FIG. 8.
Figure 10:
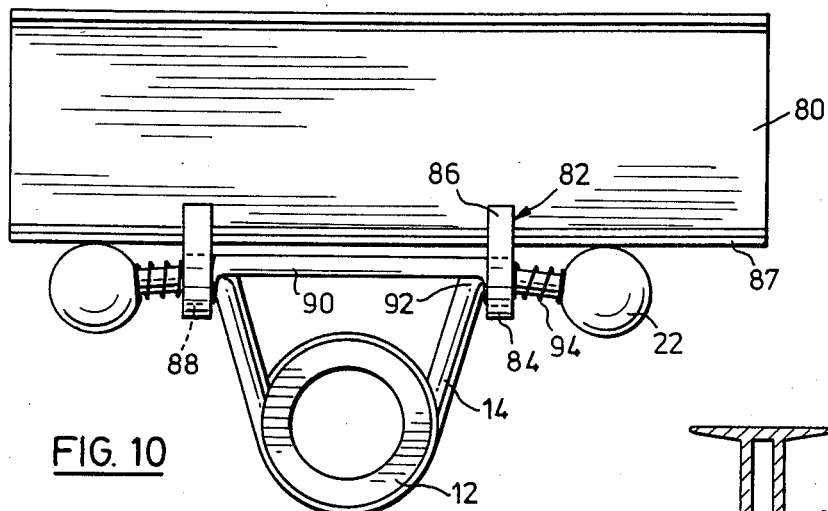
FIG. 10 is a view similar to FIG. 9 showing the trolley locked on the track.

The embodiment of FIGS. 8 to 11 operates in the same manner as the embodiment of FIGS. 1 to 6. When no weight is hung on ring 12 of trolley 81, friction elements 22 are spaced from the underside of I beam 80 as seen in FIG. 9, each friction element preferably being urged away from the I beam by the compressive action of a spring 94. In that state, trolley 81 is free to slide along I beam 80 by having hooked arms 86 slide on the upper surface of lower flange 87 of the I beam. When a weight is hung on ring 12 of trolley 81, friction elements bear against flange 87 of I beam 80 and lock the trolley in position on the I beam. The locking action is provided by a moment couple between each body 84 and its associated friction element 22.

Figure 12:
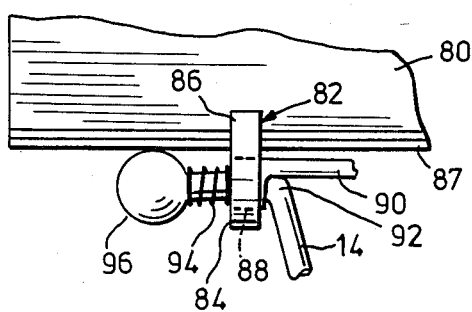
FIG. 12 is a fragmentary side view, in elevation, of an alternate embodiment of the friction element of FIGS. 8 to 11.

In the alternate embodiment shown in FIG. 12 of the drawings, spherical friction element 22 is replaced by a transverse cylindrical friction element 96 which provides an increased area of bearing surface against I beam 80 but otherwise acts in the same manner as the spherical elements of the previous embodiments.

I claim:

1. A trolley for suspending a weight from a horizontal overhead track, comprising:
    means locatable above the track and slidable along the track;
    friction means locatable below the track; and
    means interconnecting the slidable means and the friction means to suspend a weight therefrom and to provide a moment couple between the slidable means and the friction means about the track, whereby on suspension of a weight from the interconnecting means the friction means is moved towards the track to lock the trolley in any preselected position along the track.

2. A trolley as claimed in claim 1 in which the weight is detachable from the interconnecting means.

3. A trolley as claimed in claim 1 in which the track comprises a pair of spaced, parallel rails, the trolley comprising:
    a pair of arms each having annular means at one end and a friction element remote from the annular means, each arm carrying a slide member extending laterally therefrom adjacent the friction member;
    the annular means being engagable with weight supportable axle means and rotatable about the common axis thereof, the slide members being engagable with the rails and slidable along the track with the friction elements located below the track;
    the weight when supported by the axle means causing the arms to tilt and each friction element to bear upwardly against the rails to provide a moment couple with the adjacent slide member whereby the trolley is locked in a preselected position along the track.

4. A trolley as claimed in claim 3 in which the axle means comprises an annular member for receiving hook means.

5. A trolley as claimed in claim 3 in which each friction element is spherical.

6. A trolley as claimed in claim 5 in which each slide element comprises a head tapering inwardly to terminate in a shank having an eye engaged by the arm, the head being rotatable on the arm about the axis of the eye.

7. A trolley as claimed in claim 3 in which each arm has a loop and said one end to form the annular means.

8. A trolley as claimed in claim 7 in which the axle means comprises a ring having a circumscribing recess, the loops of the arms being accommodated in the recess of the ring.

9. A trolley as claimed in claim 3 in which the track has a pair of spaced, parallel rails, the rails being angled upwardly and inwardly to define a slot, a weight when supported by the trolley causing the arms of the trolley to tilt and each friction element to wedge upwardly between the inturned flanges of the rails.

10. A trolley as claimed in claim 9 in which each slide element comprises a head tapering inwardly to terminate in a shank having an eye engaged by the arm, the tilt of the arms causing each head to wedge downwardly between the rails.

11. A trolley as claimed in claim 3 in which each friction member is cylindrical.

12. A trolley as claimed in claim 3 in which each arm is angled away from the track adjacent the slide member.

13. In a hanger for suspension from an overhead track having a pair of spaced, parallel rails, a trolley comprising:
   a pair of arms each having annular means at one end and a friction element remote from the annular means, each arm carrying a slide member extending laterally therefrom adjacent the friction member;
   the annular means being rotatable about axle means mounted on the hanger, the slide members being engagable with the rails and slidable along the track with the friction elements located below the track;
   the weight of the hanger causing the arms to tilt and each friction element to bear upwardly against the rails to provide a moment couple with the adjacent slide member whereby the trolley is locked in a preselected position along the track.

14. A trolley as claimed in claim 1 in which the track comprises an I beam having an upper flange and a lower flange, the trolley comprising:
   a pair of arms each having annular means at one end and a friction element remote from the annular means, each arm carrying a slide member extending laterally therefrom adjacent the friction member;
   the annular means being engagable with weight supportable axle means and rotatable about the common axis thereof, the slide members being engagable with the lower flange of the I beam and slidable along the track with the friction elements located below the track;
   the weight when supported by the axle means causing the arms to tilt and each friction element to bear upwardly against the lower flange of the I beam to provide a moment couple with the adjacent slide member whereby the trolley is locked in a preselected position along the track.

15. A trolley as claimed in claim 14 in which each slide member comprises a yoke engagable with the lower flange of the I beam and a shank depending therefrom, the shank having an eye engaged by the arm.

16. A trolley as claimed in claim 14 in which each friction element is spherical.

17. A trolley as claimed in claim 14 in which each friction element is cylindrical and is positioned normal to the vertical longitudinal plane of the I beam.

18. A trolley as claimed in claim 14 in which each arm is angled away from the I beam adjacent the slide member.

19. A trolley as claimed in claim 14 including a compression coil spring coaxially mounted on each arm, the spring bearing at one end against the friction element and at the other end against the slide member.

20. In a hanger for suspension from an overhead I beam track having an upper flange and a lower flange, a trolley comprising:
   a pair of arms each having annular means, at one end and a friction element remote from the annular means each arm carrying a slide member extending laterally therefrom adjacent the friction member;
   the annular means being engagable with weight supportable axle means and rotatable about the common axis thereof, the slide members being engagable with the lower flange of the I beam and slidable along the track with the friction elements located below the track;
   the weight when supported by the axle means causing the arms to tilt and each friction element to bear upwardly against the lower flange of the I beam to provide a moment couple with the adjacent slide member whereby the trolley is locked in a preselected position along the track.

* * * * *